(12) United States Patent
Leech et al.

(10) Patent No.: US 7,560,271 B2
(45) Date of Patent: Jul. 14, 2009

(54) SEAFOOD SPOILAGE INDICATOR

(75) Inventors: Anna M. Leech, Pittsburgh, PA (US);
Jessica L. Palumbo, North Huntingdon, PA (US); Jason A. Berberich, Pittsburgh, PA (US); Keith E. LeJeune, Murrysville, PA (US)

(73) Assignee: Agentase, LLC, Pittsburgh, PA (US)

( * ) Notice: Subject to any disclaimer, the term of this patent is extended or adjusted under 35 U.S.C. 154(b) by 216 days.

(21) Appl. No.: 11/642,151

(22) Filed: Dec. 20, 2006

(65) Prior Publication Data

US 2008/0153079 A1    Jun. 26, 2008

(51) Int. Cl.
*C12N 1/34* (2006.01)
(52) U.S. Cl. .................. 435/287.4; 436/643
(58) Field of Classification Search .......... 435/4, 435/287.4; 436/643; 422/55–58
See application file for complete search history.

(56) References Cited

U.S. PATENT DOCUMENTS

| | | | |
|---|---|---|---|
| 5,565,329 A | | 10/1996 | Ohashi et al. |
| 5,965,453 A | * | 10/1999 | Skiffington et al. ......... 436/165 |
| 6,759,220 B1 | * | 7/2004 | LeJeune et al. ............. 435/175 |
| 6,762,213 B2 | * | 7/2004 | Lejeune et al. .............. 521/164 |
| 6,897,035 B1 | | 5/2005 | Csoregi et al. |

FOREIGN PATENT DOCUMENTS

| | | |
|---|---|---|
| JP | 60188096 | 9/1985 |
| JP | 1119752 | 5/1989 |
| JP | 3180200 | 8/1991 |
| JP | 4234997 | 8/1992 |
| JP | 6133797 | 5/1994 |
| JP | 7177898 | 7/1995 |
| JP | 2001249108 | 9/2001 |

OTHER PUBLICATIONS

Lange J. et al. Enzyme Sensor Array for the Determination of Biogenic Amines in Food Samples. Anal Bioanal Chem 372:276-283, 2002.*
Hall M. et al. A Test Strip for Diamines in Tuna. J of AOAC Int 82(5)1102-8, Sep./Oct. 1999.*
Hall M. et al. A Rapid Dipstick Test for Histamine in Tuna. Food Biotechnology 9 (1-2)39-57, 1995.*
Staruszkiewicz, Walter F., et al., "Performance of Histamine Test Kits for Applications to Seafood", Presentation on Oct. 26, 2001, 4th World Fish Inspection & Quality Congress, Vancouver, B.C.
Diffchamb, "Transia Fresh Tester" brochure www.Diffchamb.com 2006.
International Search Report dated Apr. 17, 2008, International Appln. No. PCT/US2007/025624 filed Dec. 14, 2007.
Lange et al., "Enzyme Sensor Array For The Determination Of Biogenic Amines In Food Samples", Anal. Bioanal. Chem. (2002) 276-283, vol. 372.

* cited by examiner

*Primary Examiner*—Ralph Gitomer
(74) *Attorney, Agent, or Firm*—Craig G. Cochenour; Buchanan Ingersoll & Rooney PC

(57) ABSTRACT

An enzyme based nondestructive sensor for the qualitative detection of spoilage in seafood is provided wherein the sensor does not alter the physical composition of the seafood specimen. The sensor comprises a sampling matrix, at least three or more enzymes in contact with the sampling matrix, and at least one indicator compound in contact with the sampling matrix. The enzymes are capable of interacting with four target chemicals comprising putrescine, cadaverine, histamine and tyramine, which are located on the surface of the seafood specimen. The indicator compound is capable of changing the color of the sampling matrix thereby indicating a qualitative visually detectable color change. A method for the nondestructive detection of the quality of a seafood specimen at any given time and for determining the remaining usable shelf life of the seafood specimen is disclosed.

22 Claims, 2 Drawing Sheets

Figure 1. Target amines are detected on the flesh of aging tuna.

SEAFOOD SPOILAGE INDICATOR

GOVERNMENT INTEREST

Certain embodiments of this invention were made with Government support under Contract No.R44FD001605-03-1 awarded by the Food and Drug Administration. The Government has certain rights in the invention.

FIELD OF THE INVENTION

This invention relates to an enzyme based nondestructive sensor for the qualitative detection of spoilage in seafood. A method for the nondestructive detection of the quality of a seafood specimen at any given point in time is also provided.

BACKGROUND OF THE INVENTION

Fish and seafood comprise a significant portion of the diet of nearly every culture throughout the world. In the 1990's annual global per-capita consumption of seafood exceeded 20 lbs (15 lbs U.S.). This level of consumption corresponds to more than five hundred million tons of seafood being utilized on an annual basis. These levels have continued to increase in the early 2000's. Convenience and the availability of seafood products in inland areas necessitate proper storage and transport mechanisms. While rapid freezing, refrigeration, and advanced handling and processing techniques have greatly improved capacity for delivering high quality products to the consumer, there is presently no available mechanism by which distributors, wholesalers, retailers, and consumers can be assured of product freshness at the point of purchase. Deterioration of seafood during storage not only results in a reduction of quality in the food product but has significant economic and health issues. In the area of health concerns, the proliferation of bacteria in the flesh of fish and shellfish during storage lead to many forms of food-borne illness. One of the best examples is scombroid poisoning. Scombroid poisoning results from the proliferation of bacteria in the flesh of many types of fish including, abalone, amberjack, bluefish, mackerel, mahi mahi, sardines and tuna. Excreted bacterial decarboxylase enzymes act on histidine and other amino acids in fish flesh producing large quantities of histamine and other toxic byproducts. No form of end-stage processing or high temperature cooking can counteract the hazardous nature of the toxins. Scombroid poisoning remains one of the most common forms of fish poisoning, even while most incidents go unreported due to confusion of symptoms with those of other illnesses. Even with this low level of recognition, more than 5,000 cases were recorded in U.S. and Japan over a twelve year period. Scombroid poisoning is but one of dozens of food borne illnesses that can be directly attributed to improper or extended periods of seafood storage.

As consumers are faced with media reports of illnesses resulting from seafood consumption, the seafood industry must make strides to address consumer concerns. One such mechanism is the use of expiration dating on packaging materials. These dates are based upon research data for different products and are directly related the Manufacturer's Date Packaged (DP) code. In the US, the FDA requires expiration dating on all seafood products that reflect recommendations for maximum freshness and nutrient value. These dating guidelines are based upon proper storage conditions and handling techniques. While expiration dating has merit and has undoubtedly reduced consumption of spoiled food products, dating can not take into account improper storage and handling nor can it be expected to be 100% accurate on a batch to batch basis. Expiration dating has an economic impact as well. In 1998 fish and seafood sales in the U.S. supermarkets reached more than $3.8 billion. The value of those seafood products that were disposed of due to expiration dating was more than $350 million or nearly 10% of total seafood sales. No data is readily available to determine the percentage of disposed seafood that was still viable at the time of disposal.

Clearly a simple, low-cost technique to indicate the freshness level of seafood products would have great value. It could further reduce incidences of food-borne illness, rest consumer confidence in seafood quality and may improve the economics of seafood sales by reducing losses due to expiration to a bare minimum. The industry has begun to take steps to develop such a product. Several supermarket chains have begun using "freshness tags" within seafood packaging. Freshness tags are color-producing materials that undergo a color change when seafood packages are held or transported outside a fixed temperature range for an extended period of time. Freshness tags are a first step to ensuring that expiration dating has validity and provide positive feedback to the consumer. Unfortunately, tags are of limited practical utility as they have not been present with the seafood since the date of catch or harvest. They also can not provide any useful information on a sample to sample basis.

There are a number of techniques available to assess fish quality. The most common approach involves sensory methods to evaluate food characteristics by sight, smell, and touch. Trained individuals can be quite adept at evaluating seafood quality. While it is clear that sensory assessment of fish has utility, proper analysis can only be done by a well trained group of three to six assessors. While the basics of assessment can be learned during a 2-day training course, efficiency can only be gained through years of experience. The average consumer obviously does not have the aptitude to properly and critically evaluate seafood in the same manner as a trained professional.

Much research has gone into correlating sensory assessments to chemical and bacteriological laboratory data. A viable cell count after incubation of fish flesh or direct microscopic analyses of food products are common approaches to assessing the degree of bacterial activity on a seafood product. Drawing a correlation between bacterial activity and spoilage is non-trivial, as much of the bacterial flora present on fish has no impact on spoilage. An accurate assessment of "spoilage potential" must be conducted to give viable cell counts definitive meaning. Unfortunately laboratory assessments are expensive, time consuming, and usually destroy the food sample. Typical chemical analysis involves either extraction of seafood with organic solvents and subsequent GC/HPLC analysis and identification of off-gassing volatile chemicals. Simultaneous chemical analyses during microbial cell counts have shown that many chemical markers are indicative of microbial contamination and can potentially be used to track spoilage. The literature is full of reports describing correlations between different chemical markers and seafood quality. These markers include a variety of amines, hypoxanthine, trimethylamine, ammonia, total volatile bases, ethanol, histamine, and hydrogen sulfide. Unfortunately, there are no clear trends in the literature and one study often contradicts others with respect to which chemical indicators provide correlations to quality in multiple species.

SUMMARY OF THE INVENTION

The present invention provides an enzyme based nondestructive sensor for the qualitative detection of spoilage in seafood. The sensor is nondestructive since its use does not alter the physical properties of the seafood specimen. The sensor comprises a sampling matrix, at least three or more enzymes in contact with the sampling matrix, the enzymes capable of interacting with four target chemicals comprising putrescine, cadaverine, histamine and tyramine, which are found on the surface of the seafood, and at least one indicator compound in contact with the sampling matrix. The sampling matrix is used to wipe the surface of the fish and the indicator compound is capable of changing the color of the sampling matrix, thereby indicating a qualitative visually detectable color change concerning a reaction of the enzymes with the target chemicals due to decomposition of a seafood specimen when the enzymes, the indicator compound, the sampling matrix and the seafood specimen are applied to each other.

In another embodiment of this invention, the senor includes wherein the enzymes are located within the sampling matrix. Another embodiment provides the sensor of the present invention wherein the indicator compound is located within the sampling matrix.

Another embodiment of this invention provides wherein the sensor comprises a housing wherein the sampling matrix is located in juxtaposition to the housing and in operative communication with the housing. The enzymes and the indicator compound are located within the housing.

Another embodiment of the sensor of the present invention includes a removable membrane in juxtaposition to and in communication with at least one end of the sampling matrix. The removable membrane is made of, for example but not limited to, nylon, filter paper, liner fiber, flax, unbleached cotton muslin, hemp fabric, virgin wood fiber, nitrocellulose, and cellulose acetate rayon paper The enzymes employed in the sensor of this invention comprise diamine oxidase, monoamine oxidase, and peroxidase. The indicator compound is a dye that changes optical properties along a continuum depending on the assessed quality of said seafood specimen. The dye is, for example but not limited to: oxidation-reduction dyes, Trinder Reagent(s), 10-Acetyl-3,7-dihydroxyphenoxazine, 3-(4,5-dimethylthiazol-2-yl)-2,5-diphenyltetrazolium bromide, and 2-methoxyphenol. The sampling matrix is made of, for example but not limited to, cellulose, polyurethane, polyethylene, cotton, rayon, a polymer comprising a polyester and a polyamide blend, and combinations thereof.

In a preferred embodiment of this invention, the sensor includes wherein the enzymes are in an aqueous liquid, and wherein the indicator compound is in an aqueous liquid.

In another embodiment of this invention, the sensor comprises a chamber that is located within the housing and in operative communication with the sampling matrix. The enzymes and the indicator compound are located within the chamber and are capable of being delivered to the sampling matrix simultaneously. More preferably, the sensor of this invention comprises at least two chambers, each of the chambers located within the housing and in operative communication with the sampling matrix. The enzymes are located within the first chamber and wherein the indicator compound is located within the second chamber. Most preferably, the sensor of the present invention comprises at least two chambers, each of the chambers located within the housing and in operative communication with the sampling matrix, and wherein the enzymes and the indicator compound are located in one chamber and wherein another chamber contains a wetting solution.

In yet another embodiment of the sensor of the present invention as described herein, the sensor includes wherein the enzymes are immobilized within the sampling matrix, or wherein the indicator compound is immobilized within the sampling matrix, or combinations thereof, such that the enzymes and the indicator compound are immobilized within the sampling matrix.

In another embodiment of this invention, the sensor comprises wherein the enzymes are lyophilized, or wherein the indicator dye is lyophilized, or combinations thereof. Preferably, the senor comprises wherein the enzymes and the indicator dye are lyophilized within a carrier located within the housing, wherein the carrier is in operative communication with (a) a water source capable of delivering water to the lyophilized enzymes and the lyophilized indicator dye, and (b) the sampling matrix, such that the lyophilized enzymes and lyophilized indicator compound may be reconstituted with the water from the water source and delivered to the sampling matrix.

Another embodiment of the present invention provides for a method for the nondestructive detection of the quality of a seafood specimen at any given time. This method comprises supplying a seafood specimen to be tested, wiping the seafood specimen with a sampling matrix of the sensor of the present invention as described herein. The sensor further comprises three or more enzymes in contact with the sampling matrix. The enzymes capable of interacting with four target chemicals comprising putrescine, cadaverine, histamine and tyramine, which are present on the surface of the seafood. The sensor's indicator compound that is in contact with the sampling matrix is capable of changing the color of the sampling matrix thereby indicating a qualitative visually detectable color change concerning a reaction of the enzymes with the target chemicals due to decomposition of a seafood specimen when the enzymes, the indicator compound, the sampling matrix and the seafood specimen are applied to each other. The method comprises detecting whether there is a color change in the sampling matrix, and comparing the detected color change, if any, to a reference color for establishing the quality of the seafood. If a color change occurs once the sampling matrix has sampled the seafood, the seafood is defined herein as a low quality seafood specimen or that it will be a low quality seafood specimen in a few days (about 1 to 3 days, for example). However, if after sampling the seafood specimen, the sampling matrix does not turn color, the seafood specimen is defined herein as a high quality seafood specimen and that it will remain so for at least 5 days.

In another embodiment, the method includes removing the sensor's optional removable membrane from the sampling matrix prior to detecting whether there is a color change in the sampling matrix after sampling the seafood.

In yet another embodiment of the method of the present invention, the method comprises determining the remaining usable shelf life of the seafood for human consumption based upon the color comparison.

DETAILED DESCRIPTION OF THE INVENTION

One embodiment of this invention provides an enzyme based nondestructive sensor for the qualitative detection of spoilage in seafood. Due to the lack of consensus in the literature, the applicants of the present invention have undertaken two parallel tracks of research. We first developed our own correlations of spoilage indicating chemicals and seafood quality in the three largest selling products in the US seafood industry, namely, tuna, salmon, and shrimp. The chemical indicators were monitored using standard laboratory analytical equipment and protocols. One or more of the applicants completed training courses offered by National Oceanic & Atmospheric Administration (NOAA), U.S. Department of Commerce and have become certified seafood inspectors. Chemical production in aging fish was correlated to sensory grades from the inspectors. The applicants simultaneously utilized its experience with enzyme chemistries and sensor development to devise the sensors of the present invention. One of the sensors of the present invention is a sponge-like swab that change color in response to exposure to target chemicals found on the surface of seafood. In a multitude of experimental trials, we have successfully demonstrated that the sensors of the present invention can be used to directly indicate the quality of aging seafood and determine how many days of high quality shelf life remain.

Figure 2:
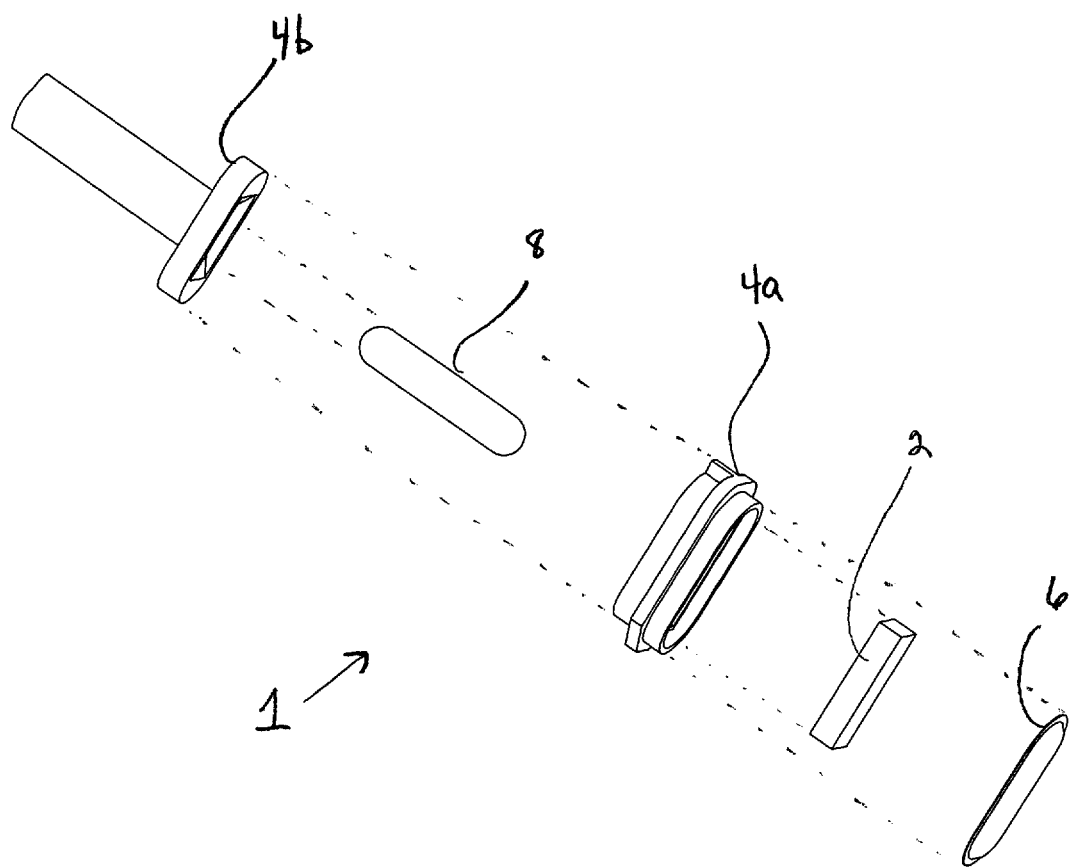
FIG. 2 is a schematic of one example of the seafood spoilage indicator (sensor) of the present invention.

The enzyme based nondestructive sensor (indicated as reference number 1, FIG. 2) for the qualitative detection of spoilage in seafood of the present invention comprises a sampling matrix (indicated as reference number 2, FIG. 2); at least three or more enzymes (not shown in FIG. 2) in contact with the sampling matrix, the enzymes capable of interacting with four target chemicals comprising putrescine, cadaverine, histamine and tyramine; and at least one indicator compound (not shown in FIG. 2) in contact with the sampling matrix, wherein the indicator compound is capable of changing the color of the sampling matrix thereby indicating a qualitative visually detectable color change concerning a reaction of the enzymes with the target chemicals due to decomposition of a seafood specimen when the enzymes, the indicator compound, the sampling matrix and the seafood specimen (not shown in FIG. 2) are applied to each other. The enzyme based sensor of this invention comprises wherein the enzymes are located within the sampling matrix. The enzyme based sensor of this invention comprises wherein the indicator compound is located within the sampling matrix.

In a preferred embodiment of this invention, the sensor as described herein comprises a housing (indicated as reference numbers 4a and 4b, FIG. 2) wherein the sampling matrix is located in juxtaposition to the housing and in operative communication with the housing, and wherein the enzymes are located within the housing, and wherein the indicator compound is located within the housing.

In an optional embodiment of the present invention, the sensor comprises a removable membrane (indicated as reference number 6, FIG. 2) in juxtaposition to and in communication with at least one end of the sampling matrix.

The enzymes comprise diamine oxidase, monoamine oxidase, and peroxidase. The indicator compound is a dye that changes optical properties along a continuum depending on the assessed quality of said seafood specimen. The dye, for example but not limited to, is selected from the group consisting of oxidation-reduction dyes, such as for example, a Trinder Reagent(s), 10-Acetyl-3,7-dihydroxyphenoxazine, 3-(4,5-dimethylthiazol-2-yl)-2,5-diphenyltetrazolium bromide (MTT), and 2-methoxyphenol. Examples of the Trinder reagent include the following N-Ethyl-N-(2-hydroxy-3-sulfopropyl)-3-methoxylaniline, sodium salt, dehydrate (ADOS), N-Ethyl-N-(3-sulfopropyl)-3-methoxyaniline, sodium salt, monohydrate (ADPS), N-Ethyl-N-(3-sulfopropyl)aniline, sodium salt (ALPS), N-Ethyl-N-(2-hydroxy-3-sulfopropyl)-3,5-dimethoxyaniline, sodium salt (DAOS), N-(2-Hydroxy-3-sulfopropyl)-3,5-dimethoxyaniline, sodium salt (HDAOS), N,N-Bis(4-sulfobutyl)-3,5-dimethylaniline, disodium salt (MADB), N-Ethyl-N-(2-hydroxy-3-sulfopropyl)-3,5-dimethylaniline, sodium salt, monohydrate (MAOS), N,N-Bis(4-sulfobutyl)-3-methylaniline, disodium salt (TODB), N-Ethyl-N-(2-hydroxy-3-sulfopropyl)-3-methylaniline, sodium salt, dehydrate (TOOS-EHSPT), and N-Ethyl-N-(3-sulfopropyl)-3-methylaniline, sodium salt (TOPS). Preferably, the class of dyes employed with the sensor of the present invention are the Trinder Reagents. They are a class of two component dyes that are water soluble. Upon oxidation, the two components come together to form an oxidized colored product. Trinder Reagents are a class of dyes that are well known by those persons skilled in the art. Below is a chemical description of an example of the two dye pairs (Trinder Reagents) employed in the sensor of this invention.

1) N-Ethyl-N-(2-hydroxy-3-sulfopropyl)-3,5-dimethoxyaniline, sodium salt (DAOS)
+4-aminoantipyrene→oxidized blue product

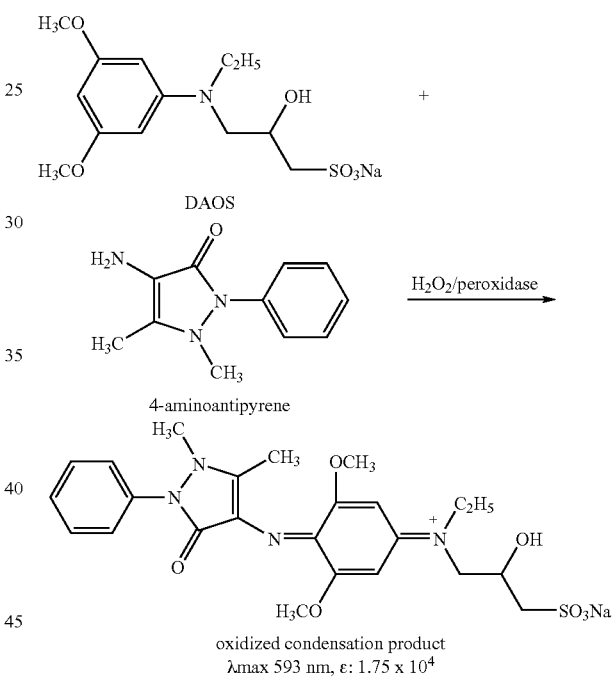

2) N-Ethyl-N-(2-hydroxy-3-sulfopropyl)-3-methylaniline, sodium salt, dehydrate (TOOS)
+4-aminoantipyrene→oxidized purple product

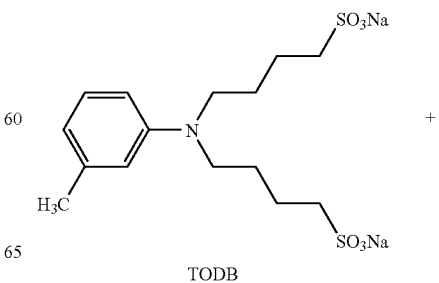

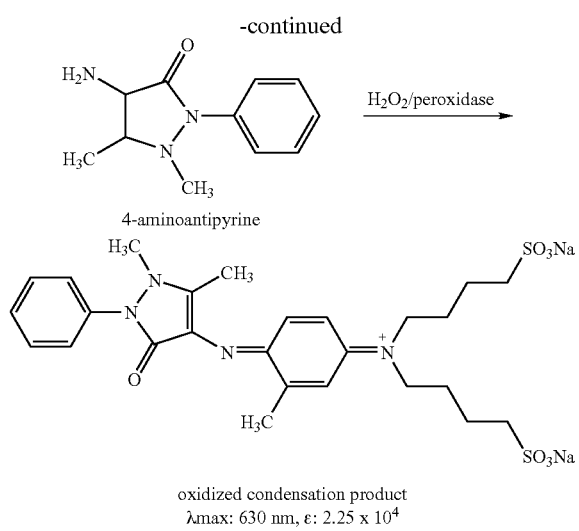

4-aminoantipyrine oxidized condensation product
λmax: 630 nm, ε: 2.25 x 10$^4$

The sampling matrix is, for example but not limited to, one selected from the group consisting of cellulose, polyurethane, polyethylene, cotton, rayon, a polymer comprising a polyester and a polyamide blend, and combinations thereof. Preferably, the sampling matrix comprises a polyurethane. The removable membrane is, for example but not limited to, selected from the group consisting of nylon, filter paper, liner fiber, flax, unbleached cotton muslin, hemp fabric, virgin wood fiber, nitrocellulose, and cellulose acetate rayon paper.

Preferably, the enzymes are in an aqueous liquid. Preferably, the indicator compound is in an aqueous liquid.

In another embodiment of the sensor of this invention, the sensor as described herein comprises a chamber (indicated as reference number 8, FIG. 2) that is located within the housing and in operative communication with the sampling matrix, wherein the enzymes and the indicator compound are located within the chamber and are capable of being delivered to the sampling matrix simultaneously. For example, but not limited to, the chamber may be a breakable glass ampoule or plastic sac or the like.

In a more preferred embodiment of this invention, the sensor as described herein comprises a at least two chambers, each of the chambers located within the housing and in operative communication with the sampling matrix, wherein the enzymes are located within the first chamber and wherein the indicator compound is located within the second chamber.

In another preferred embodiment of this invention, the sensor as described herein comprises at least two chambers, each of the chambers located within the housing and in operative communication with the sampling matrix, wherein the enzymes and the indicator compound are located in one chamber and wherein another chamber contains a wetting solution. The wetting solution may be, for example but limited to, water, a buffer solution, or any solvent that is known by those skilled in the art that is capable of reconstituting or mixing with the enzymes and indicator compound.

Another embodiment of this invention provides for the sensor as described herein wherein the enzymes are immobilized within the sampling matrix. The sensor includes wherein the indicator compound is immobilized within the sampling matrix. Preferably, the enzymes and said indicator compound are each immobilized within the sampling matrix.

In yet another embodiment of the sensor of this invention, the enzymes are lyophilized. The sensor includes wherein the indicator dye is lyophilized. Preferably, the sensor comprises wherein the enzymes and the indicator dye are lyophilized within a carrier located within the housing, wherein the carrier is in operative communication with (a) a solvent source capable of delivering the solvent to the lyophilized enzymes and the lyophilized indicator dye, and (b) the sampling matrix, such that the lyophilized enzymes and lyophilized indicator compound may be reconstituted with the solvent from the solvent source and delivered to the sampling matrix. The solvent may be for example but not limited to water, a wetting solution such as for example but not limited to a buffer solution, or any solvent that is capable of reconstituting the lyophilized enzymes and the indicator compound.

This invention also provides for a method for the nondestructive detection of the quality of a seafood specimen at any given time comprising supplying a seafood specimen to be tested, contacting the surface of a seafood specimen with a sampling matrix of a sensor, the sensor comprising the sampling matrix, at least three or more enzymes in contact with the sampling matrix, the enzymes capable of interacting with four target chemicals comprising putrescine, cadaverine, histamine and tyramine, and at least one indicator compound in contact with the sampling matrix, wherein the indicator compound is capable of changing the color of the sampling matrix thereby indicating a qualitative visually detectable color change concerning a reaction of the enzymes with the target chemicals due to decomposition of the seafood specimen when the enzymes, the indicator compound, the sampling matrix and the seafood specimen are applied to each other, detecting whether there is a color change in the sampling matrix, and comparing the detected color change, if any, to a reference color for establishing the quality of the seafood.

The method of this invention may employ any of the sensors of the present invention as described herein. For example, when the sensor includes the optional removable membrane that is in juxtaposition to and in communication with at least one end of the sampling matrix, the method includes removing the removable membrane from the sampling matrix after contacting the seafood specimen with the sampling matrix, and prior to detecting whether there is a color change in the sampling matrix.

Another embodiment of the method of the present invention as described herein comprises determining the remaining usable shelf life of said seafood for human consumption based upon the color comparison.

In yet another embodiment of this invention, the method comprises employing the sensor as described herein including wherein the housing comprises a chamber that is in operative communication with the sampling matrix, wherein the enzymes and the indicator compound are located within the chamber and capable of being delivered to the sampling matrix simultaneously.

Another embodiment of the present method as described herein includes wherein the housing comprises at least two chambers, each of the chambers in operative communication with the sampling matrix, wherein the enzymes are located within the first chamber and wherein the indicator compound is located within the second chamber.

Another embodiment of the present method as described herein includes wherein the housing comprises at least two chambers, each of the chambers in operative communication with the sampling matrix, wherein the enzymes and the indicator compound are located in one chamber and wherein another chamber contains a wetting solution.

Preferably, the method of the present invention as described herein comprises wherein the enzymes and the indicator dye are lyophilized and located with a carrier located within the housing, wherein the carrier is in operative communication with (a) a solvent or water source capable of delivering the solvent or water to the lyophilized enzymes and the lyophilized indicator dye, and (b) the sampling matrix, and including reconstituting the lyophilized enzymes and lyophilized indicator compound with the solvent or the water from the solvent source or the water source, respectively, and including delivering the reconstituted enzymes and indicator compound to the sampling matrix prior to contacting the seafood specimen with the sampling matrix of the sensor. The solvent may be for example but not limited to a wetting solution such as a buffer solution or any liquid known by those persons skilled in the art capable of reconstituting the lyophilized enzymes and indicator compound.

When a lyophilized powder is used, the enzymes and the indicator compound are each in the form of a solid that is capable of being dissolved in water. It will be understood by those skilled in the art that a solid is a phase of matter characterized by resistance to deformation and to changes in volume. A powder is a substance that has been crushed into very fine grains. It is preferable that the lyophilized powders of this invention have a particle diameter size ranging from about 50 nanometers to about 1000 nanometers. In another embodiment of this invention, the sensor provides wherein the enzyme lyophilized powder is prepared by lyophilizing a single enzyme or multiple enzymes in the presence of at least one stabilizing additive selected from the group consisting of a stabilizing polymer, a sugar, and combinations thereof. In yet another embodiment of this invention, the sensor provides wherein the lyophilized powder of the enzymes are prepared by lyophilizing multiple enzymes individually and by mixing the individually lyophilized enzyme powders together to obtain a mixture of the powdered enzymes.

Experimental Procedures

The applicants' analysis of chemicals produced when seafoods age found many of the same indicators mentioned in the literature. While volatile chemicals such as alcohols and ammonia were produced in large quantities in some species, they were not observed in any significant quantities in others. The applicants also found that the nature of some of the chemicals produced in aging seafood is a function of temperature. In many cases chemicals that were produced when the fish was stored on ice were dramatically different when aging temperatures increase by just a few degrees. The applicants' analysis did, however, identify three chemicals that correlate to quality in tuna, salmon, and shrimp (both cooked and raw) when stored over a broad range of temperatures.

The applicants periodically examined the seafood as it was aged at different temperatures (such as for example, frozen at about zero degree Centigrade or lower, refrigerated at temperatures from about freezing to below room temperature, and at room temperature at about 20 degrees Centigrade or above). The quality examination of the aging seafood was performed by a certified seafood inspector. The inspector's assessment was based upon the standard approaches employed at seafood screening facilities. The evaluation process, called sensory grading, is an organoleptic technique in which an inspector categorizes seafood based upon odor, appearance, texture and taste. The categories, in order of decreasing quality are High Pass, Mid Pass, Borderline Pass, Borderline Fail, Mid Fail and Strong Fail. Mid- and strong-failing grades are not suited for sale/use with consumers, as they will elicit strongly negative responses. Each time a seafood sample was inspected, the same sample was analyzed for target chemical analytes using standard analytical laboratory techniques including gas chromatography, GC/MS, and high performance liquid chromatography.

Figure 1:
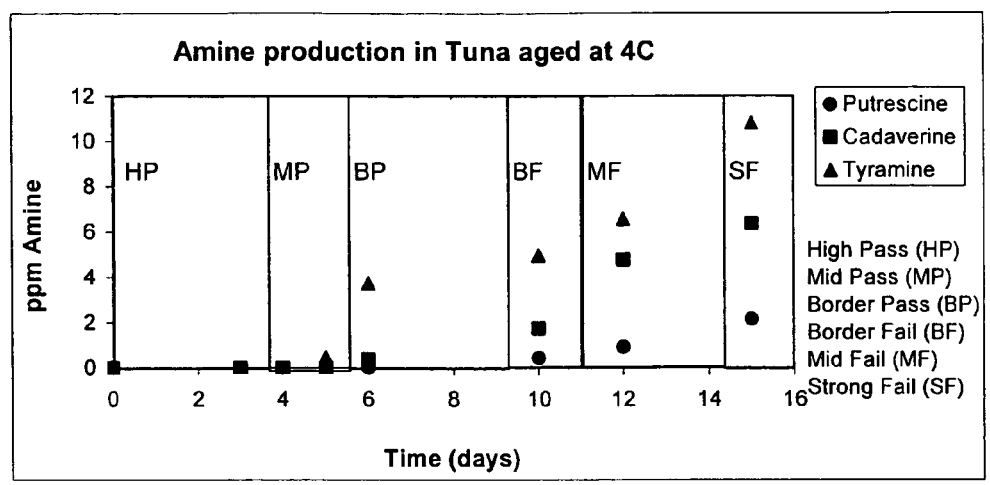
FIG. 1 is a schematic that shows target amines detected on the flesh of aging tuna fish.

As described above, many chemicals are produced as seafoods age. Most, however, can not be directly correlated to quality in different species or when seafoods age at different temperatures. The applicants' study did identify three chemical indicators that do correlate nicely with sensory grades for multiple species at different temperatures. FIG. 1 illustrates the changes in tuna stored in the refrigerator at a temperature of about 4 degrees Centigrade. FIG. 1 shows the results from sensory grading of the tuna. FIG. 1 charts amounts of putrescine, cadaverine, and tyramine collected from the flesh of the fish with the swab sensor of this invention. Notice that there are no detectable levels of these chemicals present until the tuna approaches a borderline passing grade. Also note that the seafood did not reach a mid-failing grade for ~5 days after the chemicals were detected. The same trend was also observed with salmon and shrimp (cooked and raw) at multiple storage temperatures. The borderline pass region is of significant importance as all properly refrigerated seafoods exhibited acceptable quality for several days (about 1 to 3 days, for example). It is extremely difficult for an untrained individual to distinguish the slight differences between the passing and borderline failing grades. Therefore a sensor capable of identifying subtle differences in seafood quality has utility in ensuring a shelf life of defined quality.

Applicants devised the swab-like sensor of the present invention that changes color when in contact with low levels of putrescine, cadaverine, and tyramine. Several solutions of the target amine compounds were prepared using method known by those skilled in the art. The amine concentrations of the solutions represent those previously identified within aging tuna at different sensory grades. The solutions were applied to a sampling matrix of urethane polymers synthesized by applicants in the form of urethane foam pads. Synthesis of urethane polymers is known by those skilled in the art. Enzyme-based reactions in the urethane polymer pads of this invention trigger the development of color in those samples carrying sufficient quantities of amines. The color of the urethane polymer pads a few minutes after the solutions were applied showed that as the seafood quality decreases the color response darkens. The enzyme-urethane polymer pads of this invention turn a darker color in response to increasing concentrations of putrescine, cadaverine and tyramine. Sensors that wiped high pass and mid pass tuna remain white, while sensors that wiped borderline pass and borderline fail tuna produce a light to a medium color response. Sensors that wiped mid and strong fail tuna produce a dark color response.

Applicants conducted batteries of tests comparing color development in enzyme-based sensors of the present invention to the quality of sampled fish. One such test shows contrasting colors developed when different grades of salmon fillets are screened. Sampling the low quality (or strong fail) salmon produced color development in the enzyme-urethane polymer pad within a few seconds, while the high quality fish sensor remained white. Similar results were observed with high and low quality shrimp (both cooked and raw) and tuna.

Table 1 represents recent trials of aging seafood while simultaneously monitoring quality decline via sensory grading and the sensors of the present invention. In this test only high quality seafood was purchased and refrigerated for subsequent evaluation. Every day thereafter samples were removed from the refrigerator and evaluated. The day 0 grade indicates the state of the fish on the day it was purchased. Sensory grades within Table 1 that have a + (plus) sign following them represent samples that triggered a color change in the sensors of this invention. Again, a mid-fail grade indicates that the seafood quality has deteriorated to a point at which it should no longer be consumed.

TABLE 1

Decline in Quality of Fresh Atlantic Salmon and Frozen Yellowfin Tuna Stored at 4° C. (High Pass- HP, Mid Pass- MP, Borderline Pass- BP, Borderline Fail- BF, Mid Fail- MF, Strong Fail- SF).

| Salmon | Day 0 | Day 1 | Day 2 | Day 3 | Day 4 | Day 5 | Day 6 | Day 7 |
|---|---|---|---|---|---|---|---|---|
| Trial 1 | MP | MP | BP+ | BF+ | BF+ | MF+ | MF+ | MF/SF+ |
| Trial 2 | HP/MP | MP | BF+ | BF+ | BF+ | BF+ | MF+ | MF+ |
| Trial 3 | HP | MP/BP+ | BP+ | BF+ | BF+ | BF+ | MF+ | MF+ |
| Trial 4 | HP/MP | MP/BP+ | BP+ | BF+ | BF+ | MF+ | MF+ | SF+ |

| Tuna | Day 0 | Day 1 | Day 2 | Day 3 | Day 4 | Day 5 | Day 6 | Day 7 | Day 8 | Day 9 | Day 10 | Day 11 |
|---|---|---|---|---|---|---|---|---|---|---|---|---|
| Trial 1 | MP | MP | MP | MP/BP | MP/BP+ | BP+ | BP+ | BP+ | BF+ | BF+ | BF/MF+ | MF+ |
| Trial 2 | MP | MP | MP | MP | MP/BP+ | BP+ | BP+ | BP+ | BF+ | BF+ | BF+ | MF+ |
| Trial 3 | MP | MP | MP | MP | BP+ | BP+ | BP+ | BP+ | BF+ | BF+ | BF+ | MF+ |

In each case, as the seafood declined from mid-pass through borderline pass, the seafood quality sensors of the present invention turned color because of the presence of spoilage-indicating chemicals. These types of results have been consistent through a multitude of trials. Applicants have found that the sensors of the present invention consistently change color when seafoods approach the borderline pass region and all failing sensory grades of seafood trigger strong color development. It is important to note that no color changes occur when seafoods are of high quality (having at least 5 days of usable shelf life), and 5 days pass before the seafood reaches a mid-failing grade in any case in which our sensor provided a clean result. These results suggest that the sensors of the present invention can be used to ensure consumers that seafoods will have 5 days or more of high-quality shelf life from the date of the test In one embodiment of the present invention, the sensors convey the quality of seafood by changing color. As described herein, the sensor may be in the form of a simple swab-like device that is wiped across the flesh of a sample of seafood without impacting the sample in a negative way. The swab will take on one of two colors to indicate the quality of the seafood. One color will suggest that the sample is of high quality and will remain of moderate to high quality for 5 days when properly refrigerated. The other color will tell a customer not to accept the seafood product, as it is either already of substandard quality or will be within the next few days.

The following are further examples of the embodiments of the sensors of this invention.

EXAMPLE 1

An enzyme based nondestructive sensor for the detection of spoilage indicators (Putrescine, Cadaverine, Histamine and Tyramine) in Salmon:

A) Preparation of enzymes powder: A predetermined unit activity of Monoamine Oxidase, Diamine Oxidase, and Peroxidase (1, 75, 108) is mixed together and dissolved in a sufficient amount of Potassium Phosphate Buffer pH 7.5 (50 mM). Unit activity of monoamine oxidase is defined herein as one unit of monoamine oxidase is the amount of enzyme that will oxidize 1 micromole of tyramine to p-hydroxyphenylacetaldehyde and hydrogen peroxide per minute at pH 7.5 at 37 degrees Centigrade (C) under the specific assay conditions. Unit activity of diamine oxidase is defined as the amount of enzyme that will cause the formation of 1 micromole of hydrogen peroxide from putrescine per minute at pH 8.0 at 30 C under the specific assay conditions. Unit activity of peroxidase is defined as the amount of enzyme that will form 1.0 mg purpurogallin from pyrogallol in 20 sec at pH 6.0 at 20 C under the specific assay conditions. The enzyme solution is cooled by snap freezing in liquid nitrogen and lyophilized for 1 day to obtain dry enzyme powder.

B) Preparation of indicator dye powder: Predetermined molar concentrations of indicator dyes N-Ethyl-N-(2-hydroxy-3-sulfopropyl)-3-methylaniline (2 mM) and 4-aminoantipyrine (2 mM) (used in a 1:1 ratio) are dissolved in Potassium Phosphate Buffer (50 mM). The indicator dyes were cooled by snap freezing in liquid nitrogen and lyophilized for 1 day to obtain dry indicator dye powder. Alternatively, the indicator dyes can be lyophilized separately and individual powder can be mixed together. Alternatively, the indicator dye solution can be lyophilized in the presence of the enzyme solution.

C) Preparation of sampling matrix: The sampling matrix is comprised of a polyurethane polymer and is fitted with the removable membrane as described herein. Using predetermined methods known by those skilled in the art, potassium phosphate buffer and Hypol 3000 (1.25:1) were stirred for 15 seconds at 2500 rpm with a custom-designed mixer head, internally made at ICx-Agentase. The removable membrane is made of virgin wood fiber and is used to cover the polyurethane polymer.

D) Sampling salmon with the nondestructive sensor for the detection of spoilage indicators: Sampling matrix was pre-moistened with water. The sampling matrix is then used to wipe the surface of a piece of salmon (from 2 inches by 2 inches to a whole fillet). The salmon should be wiped in a back and forth and up and down motion while applying little pressure. The wiping technique and sampling matrix will cause no physical damage to the piece of fish. The enzyme powder and indicator dye powders were reconstituted in liquid (water) and combined. The cover membrane is removed from the sampling matrix and the reconstituted enzyme/indicator dye solution is added to the polyurethane polymer. The sensor will remain white if no spoilage indicators are present and turn purple in the presence of spoilage indicators.

E) Detection of spoilage indicators in salmon: When sampling low quality salmon, the polyurethane polymer turned from white to purple. When sampling high quality salmon the polyurethane polymer remained white. A purple color change occurs when spoilage indicators are present on the salmon. While not wishing to be bound by any particular theory, applicants believe that this is due to the oxidation of N-Ethyl-N-(2-hydroxy-3-sulfopropyl)-3-methylaniline and 4-aminoantipyrine by peroxidase and hydrogen peroxide. Hydrogen peroxide is a product of the diamine oxidase, monoamine oxidase reaction with spoilage indicators. Table 2, represents data obtained when salmon was evaluated from purchase until a low quality grade is reached. Notice that when the salmon is of high quality the sensor remains white. There is no color change until the salmon reaches a borderline pass region.

TABLE 2

Decline in Quality of Fresh Atlantic Salmon Stored at 4° C. (High Pass- HP, Mid Pass- MP, Borderline Pass- BP, Borderline Fail- BF, Mid Fail- MF, Strong Fail- SF).

| Salmon | Day 0 | Day 1 | Day 2 | Day 3 | Day 4 | Day 5 | Day 6 | Day 7 |
|---|---|---|---|---|---|---|---|---|
| Sensory Grade | HP/MP | MP/BP | BP | BF | BF | MF | MF | SF |
| Sensor Color | White | Light Purple | Purple | Purple | Purple | Purple | Dark Purple | Dark Purple |

Example 2

An enzyme based nondestructive sensor for the detection of spoilage indicators (Putrescine, Cadaverine, Histamine and Tyramine) in Tuna:
  A) Tuna was sampled using the exact enzyme powder (example 1-A), indicator dye powder (example 1-B), and sampling matrix (example 1-C) that is described above.
  B) Sampling tuna with the nondestructive sensor for the detection of spoilage indicators: Sampling matrix was pre-moistened with water. The enzyme powder and indicator dye powders were reconstituted in liquid (water) and combined. The sampling matrix is then used to wipe the surfaces of a piece of tuna (from 2 inches by 2 inches to a whole tuna steak). The tuna should be wiped in a back and forth and up and down motion while applying little pressure. The wiping technique and sampling matrix will cause no damage to the piece of fish. The cover membrane is removed from the sampling matrix and the reconstituted enzyme/indicator dye solution is added to the polyurethane polymer for the detection of spoilage indicators.
  C) Detection of spoilage indicators in tuna: As in salmon, when sampling high quality tuna the sensor remained white. When the sensory grade of tuna reached the borderline pass region, the sensor turned from white to purple, indicating the presence of spoilage indicators found on the surface of the sample. Table 3 represents data obtained when tuna was studied from initial purchase until a low quality grade was reached. Tuna was stored at 4 degrees Centigrade (4° C.) and evaluated daily by sensory grade and sensor color development.

Example 3

An enzyme based nondestructive sensor for the detection of spoilage indicators (Putrescine, Cadaverine, Histamine and Tyramine) in Shrimp (both raw and cooked):

A) Shrimp (both raw and cooked) was evaluated using the same enzyme powder (example 1-A), indicator dye powder (example 1-B) and sampling matrix (example 1-C) that is described above.

B) Sampling shrimp (both raw and cooked) with the nondestructive sensor for the detection of spoilage indicators: Sampling matrix was pre-moistened with water. The enzyme powder and indicator dye powders were reconstituted in liquid (water) and combined. The sampling matrix is then used to wipe two pieces of shrimp with both shells on and off. The shrimp should be wiped in all directions while applying little pressure. The wiping technique and sampling matrix will cause no damage to the shrimp. The removable membrane is removed from the sampling matrix and the reconstituted enzyme/indicator dye solution is added to the polyurethane polymer for the detection of spoilage indicators.

C) Detection of spoilage indicators in shrimp (both raw and cooked): Similar results were seen for both raw and cooked shrimp. As in salmon and tuna, when high quality shrimp was evaluated no color change occurred. When low quality shrimp was evaluated the sensor turned purple. Spoilage indicators were not found on the shrimp until a borderline pass grade was reached. Table 4, represents data that was collected when raw white shrimp was evaluated daily from purchase until a low quality grade was reached.

TABLE 3

Decline in Quality of Frozen Yellowfin Tuna Stored at 4° C. (High Pass- HP, Mid Pass- MP, Borderline Pass- BP, Borderline Fail- BF, Mid Fail- MF, Strong Fail- SF).

| Tuna | Day 0 | Day 1 | Day 2 | Day 3 | Day 4 | Day 5 | Day 6 | Day 7 | Day 8 | Day 9 | Day 10 | Day 11 |
|---|---|---|---|---|---|---|---|---|---|---|---|---|
| Sensory Grade | MP | MP | MP | MP | MP/BP | BP | BP | BP | BF | BF | BF | MF |
| Sensor Color | White | White | White | White | Light Purple | Light Purple | Purple | Purple | Purple | Purple | Dark Purple | Dark Purple |

TABLE 4

Decline in Quality of Frozen Raw White Shrimp Stored at 4° C. (High Pass- HP, Mid Pass- MP, Borderline Pass- BP, Borderline Fail- BF, Mid Fail- MF, Strong Fail- SF).

| Shrimp | Day 0 | Day 1 | Day 2 | Day 3 | Day 4 | Day 5 | Day 6 | Day 7 | Day 8 | Day 9 | Day 10 |
|---|---|---|---|---|---|---|---|---|---|---|---|
| Sensory Grade | MP | MP | MP | MP | MP | MP/BP | BP | BP | BP | BF | MF/SF |
| Sensor Color | White | White | White | White | White | White | Light Purple | Purple | Purple | Purple | Dark Purple |

Example 4

An enzyme based nondestructive sensor for the detection of spoilage indicators can employ a variety of indicator dyes:
  A) Trinder reagents can be used to detect the presence of spoilage indicators in seafood: An assortment of Trinder reagents can be utilized to produce a color change in the presence of spoilage indicators. Trinder reagents are oxidized in the presence of hydrogen peroxide and peroxidase to produce a visible color change. The dyes are used in a 1:1 molar ratio with 4-aminoantipyrine (2 mM). Two examples of Trinder reagents are N-Ethyl-N-(2-hydroxy-3-sulfopropyl)-3-methylaniline which produces a clear to purple change and N-Ethyl-N-(2-hydroxy-3-sulfopropyl)-3,5-dimethoxyaniline which produces a clear to blue color change. The molar absorptivity of N-Ethyl-N-(2-hydroxy-3-sulfopropyl)-3,5-dimethoxyaniline is lower than N-Ethyl-N-(2-hydroxy-3-sulfopropyl)-3-methylaniline resulting in a less vibrant color change (the molar absorptivity of a chemical species at a given wavelength is a measure of how strongly the species absorbs light at that wavelength). The color change resulting from the oxidation of N-Ethyl-N-(2-hydroxy-3-sulfopropyl)-3-methylaniline is easier to visualize at lower substrate concentrations.
  B) 2-Methoxyphenol can be used to detect the presence of spoilage indicators in seafood: 2-Methoxyphenol is a clear to yellow liquid that turns a brown or orange/brown color when oxidized. In the presence of spoilage indicators, diamine oxidase and monoamine oxidase produce hydrogen peroxide. Hydrogen peroxide in the presence of peroxidase is converted to water and oxygen. In the presence of oxygen, 2-methoxyphenol turns color. The 2-methoxyphenol color change is weaker and more substrate is needed to produce a bright color change. A predetermined molar concentration of 2-methoxyphenol (100 mM) was dissolved in liquid (deionized water) and added to the sensor.
  C) Fluorescent dyes can be used to detect the presence of spoilage indicators in seafood: 10-Acetyl-3,7-dihydroxyphenoxazine is a highly sensitive dye for hydrogen peroxide. 10-Acetyl-3,7-dihydroxyphenoxazine reacts in a 1:1 stoichiometry with H2O2 to produce highly fluorescent resorufin. A fluorescent dye has the advantage of detecting minute quantities of substrate, however the disadvantage of using a fluorescent dye is the need for a fluorescent spectrophotometer. A predetermined molar concentration of 10-Acetyl-3,7-dihydroxyphenoxazine (0.1 mM) was dissolved in potassium phosphate buffer and added to the sensor.
  D) Detection limits of spoilage indicators using various dyes: N-Ethyl-N-(2-hydroxy-3-sulfopropyl)-3-methylaniline (TOOS), N-Ethyl-N-(2-hydroxy-3-sulfopropyl)-3,5-dimethoxyaniline (DAOS), 2-methoxyphenol, and 10-Acetyl-3,7-dihydroxyphenoxazine can be used as indicator dyes in our enzyme based nondestructive sensor. N-Ethyl-N-(2-hydroxy-3-sulfopropyl)-3-methylaniline and 10-Acetyl-3,7-dihydroxyphenoxazine produce the best color response. While, 2-methoxyphenol produced the weakest color response. Table 5 represents the detection limit for each indicator dye based on sensory grade. If a color change occurs at a specific sensory grade, a "Yes" is noted. If no color change occurs, a "No" is noted. TOOS and 10-Acetyl-3,7-dihydroxyphenoxazine are more sensitive to hydrogen peroxide detection than DAOS and 2-methoxyphenol, therefore they are able to detect spoilage indicators in lower concentrations. Using TOOS or 10-Acetyl-3,7-dihydroxyphenoxazine as an indicator dye allows a user to detect spoilage indicators when they are first produced in the seafood.

TABLE 5

Detection of spoilage indicators in seafood using various indicator dyes. "Yes" indicates a color change occurs, "No" indicates no color change is observed.

| Indicator Dye | High Pass | Mid Pass | Borderline Pass | Borderline Fail | Mid Fail | Strong Fail |
|---|---|---|---|---|---|---|
| TOOS | No | No* | Yes | Yes | Yes | Yes |
| DAOS | No | No | No | Yes | Yes | Yes |
| 2-methoxyphenol | No | No | No | No | Yes | Yes |
| 10-Acetyl-3,7-dihydroxyphenoxazine | No | No* | Yes | Yes | Yes | Yes |

*Does not produce a color change for a MP sensory grade but will produce a color change for a MP/BP sensory grade.

Example 5

Sampling seafood with the nondestructive sensor for the detection of spoilage indicators with alternate removable (cover) membranes on the sampling matrix:
  A) Various removable membranes can be used in our enzyme based nondestructive seafood sensor: The sampling matrix described in example 1-C contains a virgin wood fiber removable membrane that may be substituted with membranes of the following components; nitrocellulose, nylon, glass micro fibers, hardened ashless filter paper, or pure borosilicate glass micro fibers reinforced with woven glass cloth bonded with Polytetrafluoroethylene (PTFE). Sampling of seafood with a nondestructive sensor that contains one of the listed alternate removable cover membranes proceeds as described in examples 1-D, 2-A and 3-B.
  B) Detection limits of spoilage indicators using various removable membranes: The removable membranes used in applicants' nondestructive sensor are used to reduce the amount of pigment that comes off the seafood. The pigment could impede the color detection that occurs when spoilage indicators are present. Along with reducing the pigment that is transferred to the sensor, the removable membrane must also allow the spoilage indicators to diffuse onto the sensor. Table 6, lists the various removable membranes and their properties. The cover membranes are graded as good (acceptable), fair and poor (not acceptable) for each property. Virgin wood fiber is the current membrane of choice because it minimizes the amount of seafood pigment that transfers onto the polyurethane polymer, allows the spoilage indicators to diffuse through the membrane and onto the polymer, and maintains structural integrity (does not tear) during wiping.

TABLE 6

Properties of the removable membranes used in the sampling matrix of the enzyme based nondestructive sensor.

| Cover Membrane | Virgin Wood Fiber | Ashless Filter Paper | PTFE Membrane | Nylon | Glass Microfiber | Nitrocellulose |
|---|---|---|---|---|---|---|
| Maintains structural integrity | Good | Good | Good | Good | Good | Poor |
| Minimizes fish pigment onto polymer | Fair | Fair | Poor | Good | Fair | Poor |
| Allows diffusion of spoilage indicators | Good | Fair | Good | Poor | Poor | Fair |

Example 6

The enzyme based nondestructive sensor for the detection of spoilage indicators in seafood ensures a timeframe for quality shelf life: When the enzyme based nondestructive sensor is used as described in Examples 1, 2, and 3, the sensor is a valuable tool for determining the quality shelf life of seafood. The representative data in tables 2, 3 and 4 show that no color changes occur when seafoods are of high quality and 5 days pass before the seafood reaches a mid-failing grade in any case in which our sensor provided a clean result. These results suggest that the sensor can be used to ensure consumers that seafoods will have 5 days or more of high-quality shelf life from the date of the test. There are no detectable levels of spoilage indicators present until the seafood reaches a MP/BP grade. This region is of significant importance as all properly refrigerated seafoods continue to exhibit acceptable quality for several days.

It will be understood by those persons skilled in the art that applicants' sensor of the present invention provides a swab-like sensor that conveys the quality of seafood by changing color. A test resulting in one color suggests that the sample is of high quality and will remain of moderate to high quality for 5 days when properly refrigerated. The other color informs a customer that the seafood product is either already of substandard quality or will be substandard within the next few days. The product has performed well in many batteries of tests and results correlate closely to those assigned by certified seafood inspectors. The sensor and methods of this invention are ideally suited to use in supermarkets, grocery stores, and restaurants.

Whereas particular embodiments of the instant invention have been described for the purposes of illustration, it will be evident to those persons skilled in the art that numerous variations and details of the instant invention may be made without departing from the instant invention as defined in the appended claims.

What is claimed is:

1. An enzyme based nondestructive sensor for the qualitative detection of spoilage in seafood comprising:
    a sampling matrix;
    at least three or more enzymes in contact with said sampling matrix, said enzymes chemically react with four target chemicals comprising putrescine, cadaverine, histamine and tyramine if said target chemicals are located on the surface of said seafood specimen; and
    at least one indicator compound in contact with said sampling matrix, wherein said indicator compound is capable of changing the color of said sampling matrix thereby indicating a qualitative visually detectable color change concerning a reaction of said enzymes with said target chemicals due to decomposition of a seafood specimen when said enzymes, said indicator compound, said sampling matrix and said seafood specimen are in contact with each other without altering the physical properties of said seafood specimen.

2. The enzyme based sensor of claim 1 further comprising wherein said enzymes are located within said sampling matrix.

3. The enzyme based sensor of claim 1 further comprising wherein said indicator compound is located within said sampling matrix.

4. The enzyme based sensor of claim 1 further comprising a housing wherein said sampling matrix is located in juxtaposition to said housing and in operative communication with said housing, and wherein said enzymes are located within said housing, and wherein said indicator compound is located within said housing.

5. The enzyme based sensor of claim 4 further comprising a chamber that is located within said housing and in operative communication with said sampling matrix, wherein said enzymes and said indicator compound are located within said chamber and are delivered to said sampling matrix simultaneously.

6. The enzyme based sensor of claim 4 further comprising at least two chambers comprising a first chamber and a second chamber, each of said chambers located within said housing and in operative communication with said sampling matrix, wherein said enzymes are located within said first chamber and wherein said indicator compound is located within said second chamber.

7. The enzyme based sensor of claim 4 further comprising at least two chambers comprising a first chamber and a second chamber, each of said chambers located within said housing and in operative communication with said sampling matrix, wherein said enzymes and said indicator compound are located in said first chamber and wherein said second chamber contains a wetting solution.

8. The enzyme based sensor of claim 4 wherein said enzymes are immobilized within said sampling matrix.

9. The enzyme based sensor of claim 4 wherein said indicator compound is immobilized within said sampling matrix.

10. The enzyme based sensor of claim 4 wherein said enzymes and said indicator compound are immobilized within said sampling matrix.

11. The enzyme based sensor of claim 4 wherein said enzymes are lyophilized.

12. The enzyme based sensor of claim 4 wherein said indicator dye is lyophilized.

13. The enzyme based sensor of claim 4 wherein said enzymes and said indicator dye are lyophilized within a carrier located within said housing, wherein said carrier is in operative communication with (a) a water source capable of delivering water to said lyophilized enzymes and said lyophilized indicator dye, and (b) said sampling matrix, such that said lyophilized enzymes and lyophilized indicator compound may be reconstituted with said water from said water source and delivered to said sampling matrix.

14. The enzyme based sensor of claim 1 further comprising a removable membrane in juxtaposition to and in communication with at least one end of said sampling matrix.

15. The enzyme based sensor of claim 14 wherein said removable membrane is selected from the group consisting of nylon, filter paper, liner fiber, flax, unbleached cotton muslin, hemp fabric, virgin wood fiber, nitrocellulose, and cellulose acetate rayon paper.

16. The enzyme based sensor of claim 1 wherein said enzymes comprise diamine oxidase, monoamine oxidase, and peroxidase.

17. The enzyme based sensor of claim 1 wherein said indicator compound is a dye that changes optical properties along a continuum wherein said continuum is a change in color intensity that correlates to an acceptable or a nonacceptable quality of said seafood specimen.

18. The enzyme based sensor of claim 17 wherein said dye is selected from the group consisting of oxidation-reduction dyes, at least one Tinder Reagent, 10-Acetyl-3,7-dihydroxyphenoxazine, 3-(4,5-dimethylthiazol-2-yl)-2,5-diphenyltetrazolium bromide, and 2-methoxyphenol.

19. The enzyme based sensor of claim 1 wherein said sampling matrix comprises a polyurethane.

20. The enzyme based sensor of claim 1 wherein said sampling matrix is one selected from the group consisting of cellulose, polyurethane, polyethylene, cotton, rayon, a polymer comprising a polyester and a polyamide blend, and combinations thereof.

21. The enzyme based sensor of claim 1 wherein said enzymes are in an aqueous liquid.

22. The enzyme based sensor of claim 1 wherein said indicator compound is in an aqueous liquid.

* * * * *